US009289114B2

(12) United States Patent
Vasan

(10) Patent No.: US 9,289,114 B2
(45) Date of Patent: Mar. 22, 2016

(54) DISPOSABLE, SELF-CONTAINED LARYNGOSCOPE AND METHOD OF USING SAME

(71) Applicant: Nilesh R. Vasan, Nichols Hills, OK (US)

(72) Inventor: Nilesh R. Vasan, Nichols Hills, OK (US)

( * ) Notice: Subject to any disclaimer, the term of this patent is extended or adjusted under 35 U.S.C. 154(b) by 0 days.

(21) Appl. No.: 13/740,164

(22) Filed: Jan. 12, 2013

(65) Prior Publication Data

US 2014/0316206 A1    Oct. 23, 2014

Related U.S. Application Data

(63) Continuation-in-part of application No. 12/847,915, filed on Jul. 30, 2010.

(51) Int. Cl.
    *A61B 1/267* (2006.01)
    *A61B 1/06* (2006.01)
    *A61B 1/00* (2006.01)

(52) U.S. Cl.
    CPC ............ *A61B 1/267* (2013.01); *A61B 1/00103* (2013.01); *A61B 1/06* (2013.01); *A61B 1/0669* (2013.01); *A61B 1/0684* (2013.01)

(58) Field of Classification Search
    CPC .... A61B 1/00165; A61B 1/0684; A61B 1/07; A61B 1/267–1/2763; A61B 19/5202; A61B 2019/5206
    USPC ................. 600/185–201, 208, 212, 223, 235, 600/237–239, 245, 248
    See application file for complete search history.

(56) References Cited

U.S. PATENT DOCUMENTS

| | | | | |
|---|---|---|---|---|
| 1,292,326 A * | 1/1919 | Jacobson | ...... | 359/503 |
| 1,657,148 A * | 1/1928 | De Forest | ...... | 600/237 |
| 2,070,820 A * | 2/1937 | Allyn | ...... | 600/196 |
| 2,182,390 A * | 12/1939 | Reardon | ...... | 600/237 |
| 2,289,226 A * | 7/1942 | Von Foregger | ...... | 600/193 |
| 2,637,317 A * | 5/1953 | Martin | ...... | 600/185 |
| 2,648,329 A * | 8/1953 | Morch | ...... | 600/193 |
| 2,756,742 A * | 7/1956 | Barton | ...... | 600/205 |
| 3,261,350 A * | 7/1966 | Wallace | ...... | 600/182 |
| 3,459,178 A * | 8/1969 | Fleming | ...... | 600/248 |
| 3,507,272 A * | 4/1970 | Laerdal | ...... | 600/191 |
| 3,556,086 A * | 1/1971 | Gordon | ...... | 600/248 |
| 3,592,199 A * | 7/1971 | Ostensen | ...... | 600/198 |
| 3,595,222 A * | 7/1971 | Vellacott et al. | ...... | 600/197 |

(Continued)

OTHER PUBLICATIONS

Allison, Michael, An Update on Airway Management in Emergency Medicine, AAEM/RSA News, Resident Journal Review, CommonSense, p. 30-34 Nov./Dec. 2012.

(Continued)

*Primary Examiner* — Todd E Manahan
*Assistant Examiner* — Michelle C Eckman
(74) *Attorney, Agent, or Firm* — Dunlap Codding, P.C.

(57) ABSTRACT

The present invention is generally directed toward a laryngoscope having a handle, a rigid tube, and an optical subassembly. The handle has a distal end and a proximate end. The tube is hollow and also has a distal end having a distal opening and a proximate end having a proximate opening. The optical subassembly includes a light source located within the handle, a power source located within the handle and in communication with the light source and a light carrier extending between the handle and the tube and in communication with the light source and providing light inside and along the entire length of the tube.

9 Claims, 7 Drawing Sheets

(56) References Cited

U.S. PATENT DOCUMENTS

| | | | | |
|---|---|---|---|---|
| 3,598,113 A | * | 8/1971 | Moore et al. | 600/199 |
| 3,616,792 A | * | 11/1971 | Pleet | 600/239 |
| 3,638,644 A | * | 2/1972 | Reick | 600/191 |
| 3,716,047 A | * | 2/1973 | Moore et al. | 600/212 |
| 3,848,587 A | * | 11/1974 | McDonald | 600/187 |
| 4,166,467 A | * | 9/1979 | Abramson | 128/207.14 |
| 4,273,112 A | * | 6/1981 | Heine et al. | 600/193 |
| 4,294,235 A | * | 10/1981 | Storz | 600/187 |
| 4,306,547 A | * | 12/1981 | Lowell | 600/188 |
| 4,320,745 A | * | 3/1982 | Bhitiyakul et al. | 600/188 |
| 4,337,761 A | * | 7/1982 | Upsher | 600/188 |
| 4,360,008 A | * | 11/1982 | Corazzelli, Jr. | 600/194 |
| 4,425,909 A | * | 1/1984 | Rieser | 600/197 |
| 4,437,458 A | * | 3/1984 | Upsher | 600/193 |
| 4,527,553 A | * | 7/1985 | Upsher | 600/188 |
| 4,550,717 A | * | 11/1985 | Berger | 600/121 |
| 4,556,052 A | * | 12/1985 | Muller | 600/193 |
| 4,557,256 A | * | 12/1985 | Bauman | 600/193 |
| 4,567,882 A | * | 2/1986 | Heller | 600/249 |
| 4,583,527 A | * | 4/1986 | Musicant et al. | 600/195 |
| 4,592,343 A | * | 6/1986 | Upsher | 600/193 |
| 4,793,327 A | * | 12/1988 | Frankel | 600/194 |
| 4,799,485 A | * | 1/1989 | Furey et al. | 600/193 |
| D304,494 S | * | 11/1989 | Rosenwald et al. | D24/138 |
| 4,884,558 A | * | 12/1989 | Gorski et al. | 600/186 |
| 4,905,669 A | * | 3/1990 | Bullard et al. | 600/104 |
| 4,947,896 A | * | 8/1990 | Bartlett | 600/187 |
| 5,038,766 A | * | 8/1991 | Parker | 128/200.26 |
| 5,060,633 A | | 10/1991 | Gibson | |
| 5,237,985 A | * | 8/1993 | Hodgson et al. | 600/205 |
| 5,261,392 A | * | 11/1993 | Wu | 600/188 |
| 5,263,472 A | * | 11/1993 | Ough | 600/188 |
| 5,277,173 A | * | 1/1994 | Cantele | 600/191 |
| 5,329,938 A | * | 7/1994 | Lonky | 600/223 |
| 5,363,838 A | * | 11/1994 | George | 600/120 |
| 5,394,865 A | * | 3/1995 | Salerno | 600/199 |
| 5,402,771 A | * | 4/1995 | Pilling | 600/188 |
| 5,443,058 A | * | 8/1995 | Ough | 600/188 |
| 5,498,231 A | * | 3/1996 | Franicevic | 600/190 |
| 5,536,245 A | * | 7/1996 | Dahlbeck | 600/195 |
| 5,551,946 A | * | 9/1996 | Bullard | 600/194 |
| 5,571,071 A | * | 11/1996 | Shapiro | 600/187 |
| 5,575,758 A | * | 11/1996 | Easterbrook, III | 600/193 |
| 5,584,796 A | * | 12/1996 | Cohen | 600/201 |
| 5,603,688 A | * | 2/1997 | Upsher | 600/190 |
| 5,643,174 A | * | 7/1997 | Yamamoto et al. | 600/114 |
| 5,651,760 A | * | 7/1997 | Upsher | 600/193 |
| 5,651,761 A | * | 7/1997 | Upsher | 600/194 |
| 5,665,052 A | * | 9/1997 | Bullard | 600/194 |
| 5,688,224 A | * | 11/1997 | Forkey et al. | 600/200 |
| 5,716,329 A | * | 2/1998 | Dieter | 600/210 |
| 5,722,936 A | * | 3/1998 | Trulio | 600/243 |
| 5,733,241 A | * | 3/1998 | King | 600/114 |
| 5,743,848 A | * | 4/1998 | Koeda et al. | 600/178 |
| 5,776,052 A | * | 7/1998 | Callahan | 600/194 |
| 5,776,053 A | * | 7/1998 | Dragisic et al. | 600/195 |
| 5,785,648 A | * | 7/1998 | Min | 600/206 |
| 5,817,127 A | * | 10/1998 | Borodulin et al. | 606/198 |
| 5,827,178 A | * | 10/1998 | Berall | 600/185 |
| 5,873,818 A | * | 2/1999 | Rothfels | 600/188 |
| 5,891,018 A | * | 4/1999 | Wells | 600/226 |
| 5,893,830 A | * | 4/1999 | Zeitels | 600/190 |
| 5,897,489 A | * | 4/1999 | Urbanowicz et al. | 600/185 |
| 5,906,576 A | * | 5/1999 | Upsher | 600/178 |
| 5,984,863 A | * | 11/1999 | Ansari | 600/185 |
| 5,993,383 A | * | 11/1999 | Haase | 600/191 |
| 6,004,264 A | * | 12/1999 | Sano et al. | 600/178 |
| 6,080,105 A | | 6/2000 | Spears | |
| 6,083,151 A | * | 7/2000 | Renner et al. | 600/114 |
| 6,095,972 A | * | 8/2000 | Sakamoto | 600/190 |
| 6,106,458 A | * | 8/2000 | Ha | 600/187 |
| 6,115,523 A | * | 9/2000 | Choi et al. | 385/116 |
| 6,123,666 A | * | 9/2000 | Wrenn et al. | 600/188 |
| 6,126,594 A | * | 10/2000 | Bayer | 600/184 |
| 6,146,402 A | | 11/2000 | Munoz | |
| 6,152,873 A | * | 11/2000 | Rogers | 600/200 |
| 6,174,281 B1 | * | 1/2001 | Abramowitz | 600/196 |
| 6,176,824 B1 | * | 1/2001 | Davis | 600/178 |
| 6,322,499 B1 | * | 11/2001 | Evans et al. | 600/212 |
| 6,354,993 B1 | * | 3/2002 | Kaplan et al. | 600/188 |
| 6,425,859 B1 | * | 7/2002 | Foley et al. | 600/204 |
| 6,428,473 B1 | * | 8/2002 | Leonard et al. | 600/219 |
| 6,432,043 B2 | * | 8/2002 | Nakaichi et al. | 600/120 |
| 6,432,049 B1 | * | 8/2002 | Banta et al. | 600/249 |
| 6,471,643 B1 | * | 10/2002 | Henderson | 600/185 |
| 6,494,828 B1 | * | 12/2002 | Berall | 600/190 |
| 6,497,654 B1 | * | 12/2002 | Leonard et al. | 600/245 |
| 6,569,089 B1 | * | 5/2003 | Covington et al. | 600/199 |
| 6,655,377 B2 | * | 12/2003 | Pacey | 128/200.26 |
| 6,666,819 B2 | * | 12/2003 | Heine et al. | 600/199 |
| 6,764,443 B1 | * | 7/2004 | Watson | 600/197 |
| 6,843,769 B1 | * | 1/2005 | Gandarias | 600/189 |
| 6,890,298 B2 | * | 5/2005 | Berci et al. | 600/185 |
| 6,916,287 B2 | * | 7/2005 | Dematteis et al. | 600/184 |
| 6,955,645 B1 | * | 10/2005 | Zeitels | 600/187 |
| 7,044,909 B2 | * | 5/2006 | Berci et al. | 600/185 |
| 7,052,456 B2 | * | 5/2006 | Simon | 600/120 |
| 7,128,710 B1 | * | 10/2006 | Cranton et al. | 600/199 |
| 7,153,260 B1 | * | 12/2006 | Girgis | 600/196 |
| 7,174,889 B2 | * | 2/2007 | Boedeker et al. | 128/200.26 |
| 7,182,728 B2 | * | 2/2007 | Cubb et al. | 600/194 |
| 7,306,559 B2 | * | 12/2007 | Williams | 600/245 |
| 7,338,440 B1 | * | 3/2008 | Smith | 600/187 |
| 7,452,329 B2 | * | 11/2008 | Bastia et al. | 600/184 |
| 7,556,601 B2 | * | 7/2009 | Branch et al. | 600/245 |
| 7,874,982 B2 | * | 1/2011 | Selover et al. | 600/245 |
| 7,878,973 B2 | * | 2/2011 | Yee et al. | 600/199 |
| 7,901,353 B2 | * | 3/2011 | Vayser et al. | 600/182 |
| 7,909,758 B2 | * | 3/2011 | Shapiro | 600/190 |
| 7,951,077 B2 | * | 5/2011 | Sayeg et al. | 600/210 |
| 8,012,087 B2 | * | 9/2011 | Tenger et al. | 600/199 |
| 8,012,089 B2 | * | 9/2011 | Bayat | 600/214 |
| 8,083,672 B2 | * | 12/2011 | Minson | 600/190 |
| 8,152,719 B2 | * | 4/2012 | Tenger et al. | 600/199 |
| 8,388,523 B2 | * | 3/2013 | Vivenzio et al. | 600/178 |
| 8,414,481 B2 | | 4/2013 | Hakanen et al. | |
| 8,663,099 B2 | * | 3/2014 | Tydlaska et al. | 600/186 |
| 2002/0068854 A1 | * | 6/2002 | Heine et al. | 600/199 |
| 2002/0082478 A1 | * | 6/2002 | McGrath | 600/193 |
| 2002/0087050 A1 | * | 7/2002 | Rudischhauser et al. | 600/199 |
| 2002/0153008 A1 | * | 10/2002 | Schwartz et al. | 128/200.26 |
| 2002/0156350 A1 | * | 10/2002 | Nieto | 600/223 |
| 2003/0168059 A1 | * | 9/2003 | Pacey | 128/200.26 |
| 2004/0019256 A1 | * | 1/2004 | Cubb et al. | 600/188 |
| 2004/0079364 A1 | * | 4/2004 | Christopher | 128/200.26 |
| 2004/0127770 A1 | * | 7/2004 | McGrath | 600/193 |
| 2004/0133073 A1 | | 7/2004 | Berci et al. | |
| 2004/0210114 A1 | * | 10/2004 | Simon | 600/185 |
| 2004/0210115 A1 | * | 10/2004 | Ma et al. | 600/199 |
| 2004/0215062 A1 | * | 10/2004 | Dalle et al. | 600/193 |
| 2005/0059863 A1 | * | 3/2005 | Zilch | 600/188 |
| 2005/0065543 A1 | | 3/2005 | Kahle et al. | |
| 2005/0148821 A1 | * | 7/2005 | Berci et al. | 600/188 |
| 2005/0192481 A1 | * | 9/2005 | Berci et al. | 600/188 |
| 2005/0240081 A1 | * | 10/2005 | Eliachar | 600/199 |
| 2005/0251119 A1 | | 11/2005 | Eaton | |
| 2006/0004260 A1 | * | 1/2006 | Boedeker et al. | 600/188 |
| 2006/0074276 A1 | * | 4/2006 | Cantrell | 600/196 |
| 2006/0180155 A1 | * | 8/2006 | Glassenberg et al. | 128/207.15 |
| 2006/0183978 A1 | * | 8/2006 | Howard | 600/197 |
| 2006/0217596 A1 | * | 9/2006 | Williams | 600/245 |
| 2006/0224045 A1 | * | 10/2006 | Whipple et al. | 600/245 |
| 2006/0276693 A1 | * | 12/2006 | Pacey | 600/188 |
| 2006/0276694 A1 | * | 12/2006 | Acha Gandarias | 600/194 |
| 2007/0100210 A1 | * | 5/2007 | Selover et al. | 600/199 |
| 2007/0100211 A1 | * | 5/2007 | Selover et al. | 600/199 |
| 2007/0167686 A1 | * | 7/2007 | McGrath | 600/188 |
| 2007/0173697 A1 | * | 7/2007 | Dutcher et al. | 600/188 |
| 2007/0208226 A1 | * | 9/2007 | Grey et al. | 600/212 |
| 2007/0213594 A1 | * | 9/2007 | Nguyen | 600/190 |
| 2007/0225571 A1 | * | 9/2007 | Branch et al. | 600/245 |
| 2007/0276191 A1 | * | 11/2007 | Selover et al. | 600/245 |
| 2007/0299313 A1 | * | 12/2007 | McGrath | 600/186 |
| 2008/0051628 A1 | * | 2/2008 | Pecherer et al. | 600/112 |

(56) References Cited

U.S. PATENT DOCUMENTS

| | | | |
|---|---|---|---|
| 2008/0103364 A1* | 5/2008 | Shapiro | 600/185 |
| 2008/0108877 A1 | 5/2008 | Bayat | |
| 2008/0146879 A1* | 6/2008 | Pacey | 600/188 |
| 2008/0188717 A1* | 8/2008 | Chen et al. | 600/199 |
| 2008/0200766 A1* | 8/2008 | Ayoun et al. | 600/199 |
| 2008/0234549 A1* | 9/2008 | Geist et al. | 600/194 |
| 2008/0294010 A1* | 11/2008 | Cooper | 600/199 |
| 2008/0300464 A1* | 12/2008 | Dhingra et al. | 600/199 |
| 2009/0032016 A1 | 2/2009 | Law | |
| 2009/0036744 A1* | 2/2009 | Vayser | 600/182 |
| 2009/0065000 A1* | 3/2009 | Chen | 128/200.26 |
| 2009/0099421 A1* | 4/2009 | Shalman et al. | 600/197 |
| 2009/0182364 A1* | 7/2009 | Mettler, Jr. | 606/161 |
| 2009/0318767 A1* | 12/2009 | Tenger et al. | 600/194 |
| 2009/0318768 A1* | 12/2009 | Tenger et al. | 600/194 |
| 2009/0318769 A1* | 12/2009 | Tenger et al. | 600/199 |
| 2010/0022843 A1* | 1/2010 | Pecherer et al. | 600/197 |
| 2010/0041953 A1* | 2/2010 | Pecherer et al. | 600/193 |
| 2010/0049003 A1* | 2/2010 | Levy | 600/199 |
| 2010/0069722 A1* | 3/2010 | Shalman et al. | 600/193 |
| 2010/0114110 A1* | 5/2010 | Taft et al. | 606/108 |
| 2010/0121152 A1* | 5/2010 | Boedeker | 600/187 |
| 2010/0152541 A1* | 6/2010 | Tenger et al. | 600/194 |
| 2010/0191054 A1* | 7/2010 | Supiez | 600/109 |
| 2010/0191061 A1* | 7/2010 | Simons | 600/186 |
| 2010/0191062 A1* | 7/2010 | Kieffer | 600/199 |
| 2010/0198017 A1* | 8/2010 | Raspallo | 600/190 |
| 2010/0224187 A1* | 9/2010 | Dalton | 128/200.26 |
| 2010/0249513 A1* | 9/2010 | Tydlaska | 600/186 |
| 2010/0261967 A1* | 10/2010 | Pacey et al. | 600/186 |
| 2010/0298644 A1* | 11/2010 | Kleene | 600/188 |
| 2010/0305406 A1* | 12/2010 | Braun et al. | 600/202 |
| 2011/0021882 A1* | 1/2011 | Selover et al. | 600/245 |
| 2011/0060190 A1* | 3/2011 | Pecherer | 600/188 |
| 2011/0077466 A1 | 3/2011 | Rosenthal | |
| 2011/0092774 A1* | 4/2011 | Herman | 600/190 |
| 2011/0105848 A1* | 5/2011 | Sadovsky et al. | 600/204 |
| 2011/0130627 A1* | 6/2011 | McGrail et al. | 600/109 |
| 2011/0152620 A1* | 6/2011 | Dhonneur | 600/194 |
| 2011/0201890 A1* | 8/2011 | Rosenthal | 600/188 |
| 2012/0029292 A1* | 2/2012 | Kao et al. | 600/190 |
| 2012/0029293 A1* | 2/2012 | Vasan | 600/194 |
| 2012/0078056 A1* | 3/2012 | Tenger et al. | 600/194 |
| 2012/0095295 A1* | 4/2012 | McGrath et al. | 600/194 |
| 2012/0178997 A1* | 7/2012 | Tydlaska et al. | 600/186 |
| 2012/0245413 A1* | 9/2012 | Vayser et al. | 600/104 |
| 2012/0259176 A1* | 10/2012 | Grey et al. | 600/188 |
| 2012/0330104 A1* | 12/2012 | Tenger et al. | 600/191 |
| 2013/0006057 A1* | 1/2013 | Pastron | 600/187 |
| 2013/0006061 A1* | 1/2013 | Alexander et al. | 600/235 |
| 2013/0053647 A1* | 2/2013 | McChesney | 600/186 |
| 2013/0066151 A1* | 3/2013 | Chen | 600/188 |
| 2013/0066152 A1* | 3/2013 | Chen | 600/188 |
| 2013/0109923 A1* | 5/2013 | Trakas | 600/195 |
| 2013/0158356 A1* | 6/2013 | Yilmaz | 600/187 |
| 2013/0190558 A1* | 7/2013 | Alexander et al. | 600/37 |
| 2013/0190568 A1* | 7/2013 | Hakanen et al. | 600/186 |
| 2013/0197313 A1* | 8/2013 | Wan | 600/202 |
| 2013/0217971 A1* | 8/2013 | Boedeker | 600/188 |
| 2013/0267786 A1* | 10/2013 | Vayser et al. | 600/205 |
| 2013/0281981 A1* | 10/2013 | Shamir Lebovitz | 604/511 |
| 2013/0296653 A1* | 11/2013 | Brown et al. | 600/114 |
| 2013/0317300 A1* | 11/2013 | Berci et al. | 600/188 |
| 2013/0319406 A1* | 12/2013 | Borrye | 128/200.26 |
| 2013/0324798 A1* | 12/2013 | Molnar et al. | 600/120 |
| 2013/0338443 A1* | 12/2013 | Wu | 600/187 |
| 2013/0345518 A1* | 12/2013 | Law et al. | 600/188 |
| 2014/0018629 A1* | 1/2014 | Acha Gandarias | 600/197 |

OTHER PUBLICATIONS

Katz, Steven, Misplaced Endotracheal Tubes by Paramedics in an Urban Emergency Medical Services System, EMS/Original Contribution, Annals of Emergency Medicine, p. 32-37, Jan. 2001.

Jones, James H., Emergency Physician-Verified Out-of-hospital Intubation: Miss Rates by Paramedics, ACAD EMERG MED, p. 707-709, vol. 11, No. 6, Jun. 2004.

Saving Lives on the Battlefield; A Joint Trauma System Review of Pre-Hospital Trauma Care in Combined Joint Operating Area-Afghanistan (CJOA-A) Executive Summary, TCCC Updates, p. 77-85, Journal of Special Operations Medicine, vol. 13, Edition 1/Spring 2013.

Mabry, Robert, An Analysis of Battlefield Cricothyrotomy in Iraq and Afghanistan, p. 17-23, Journal of Special Operations Medicine vol. 12, Edition 1/Spring 2012.

Deakin, CD., Prehospital Management of the Traumatized Airway, European Journal of Emergency Medicine, Dec. 1996, vol. 3 Issue 4, pp. 233-243.

Bochicchio, GV., Is Field Intubation Useful?, Current Opinion in Critical Care, Dec. 2003; vol. 9 Issue 6, pp. 524-529.

Wang, HE, How many attempts are required to accomplish out-of-hospital endotracheal intubation?, Academic Emergency Medicine, Apr. 2006, vol. 13 Issue 4, pp. 372-377.

Cobas, MA, Prehospital Intubations and Mortality: a level 1 trauma center perspective, Anesthesia-Analgesia, Aug. 2009, vol. 109, No. 2, pp. 489-493.

Gaither, Joshua B., Prevalence of Difficult Airway Predictors in Cases of Failed Prehospital Endotracheal Intubation, the Journal of Emergency Medicine, vol. 47, No. 3, pp. 294-300, 2014.

Mhyre, Jill M., The Unanticipated Difficult Intubation in Obstetrics, Society for Obstetric Anesthesia and Perinatology, vol. 112, No. 3, Mar. 2011.

Quinn, A.C., Failed tracheal intubation in obstetric anaesthesia; 2 yr national case—control study in the UK, British Journal of Anaesthesia 110 (1): 74-80 (2013) Advance Access publication Sep. 17, 2012.

Vasdev, Gurinder M., Management of the difficult and failed airway in obstetric anesthesia, Journal of Anesthesia 22:38-48, 2008.

Office Action Summary for U.S. Appl. No. 12/847,915 mailed Aug. 11, 2015.

* cited by examiner

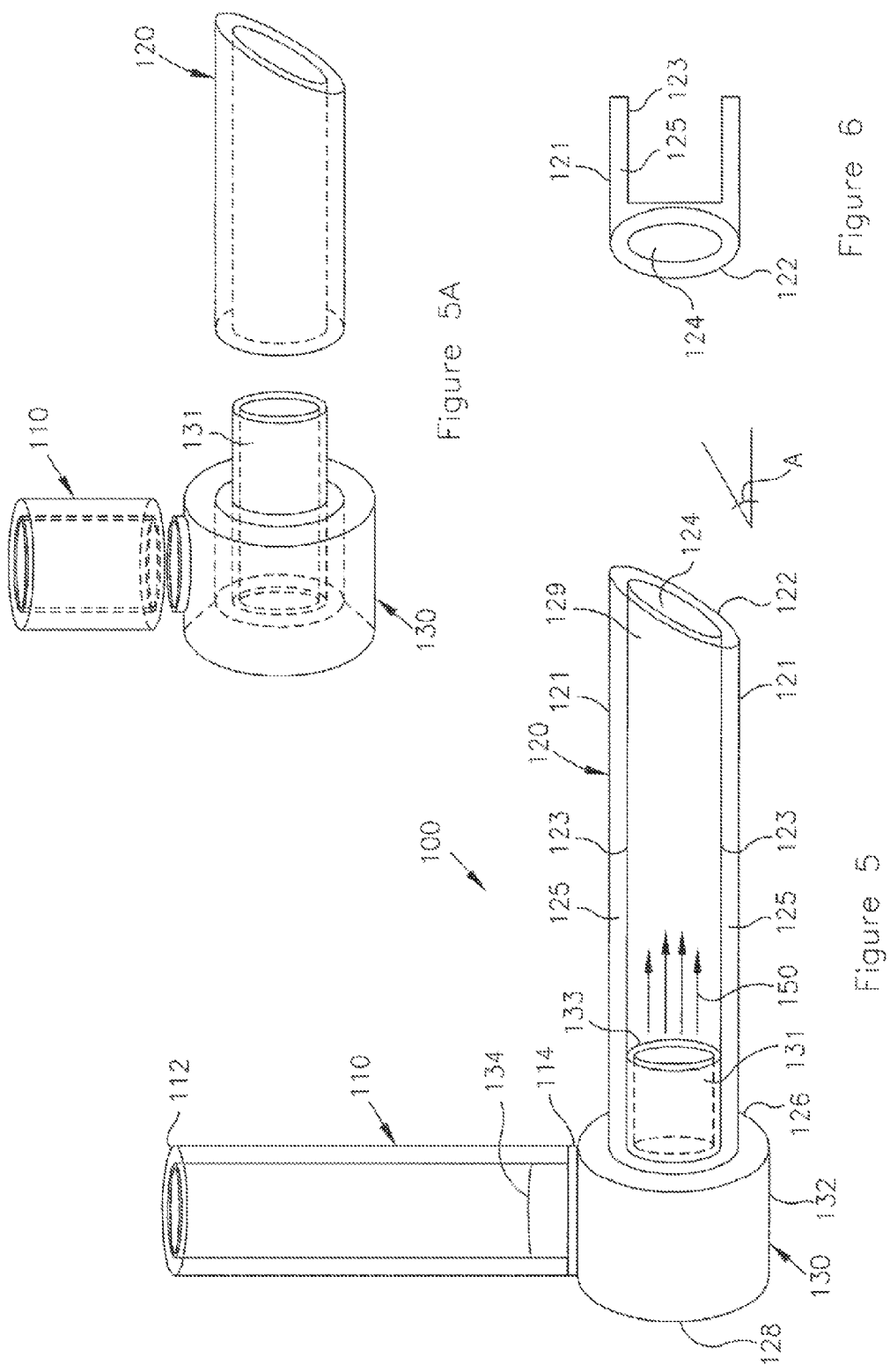

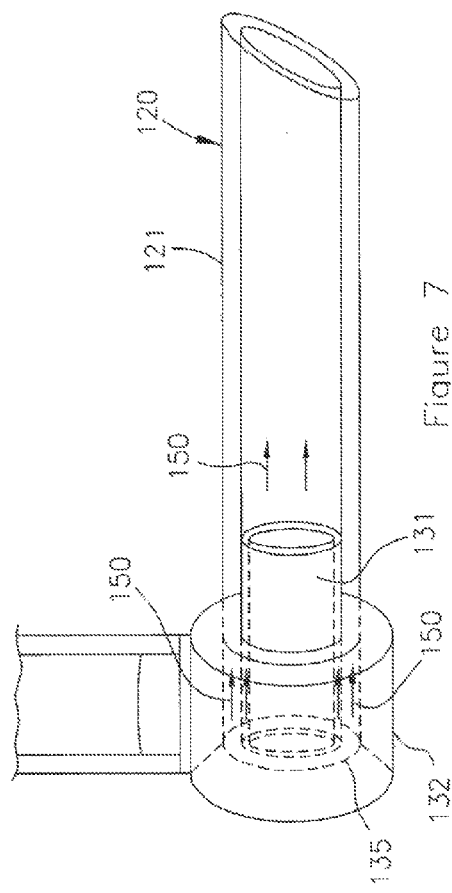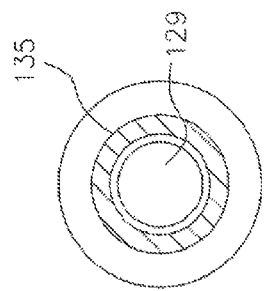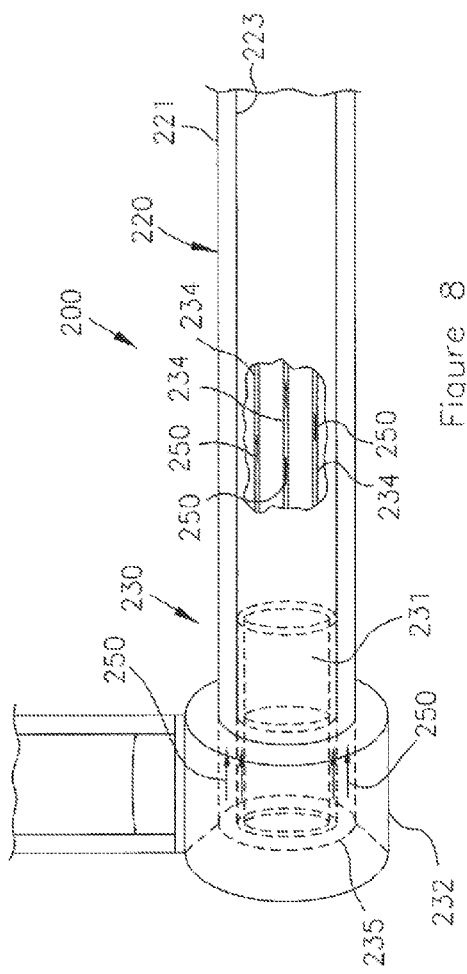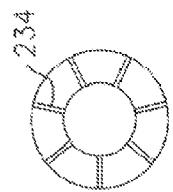

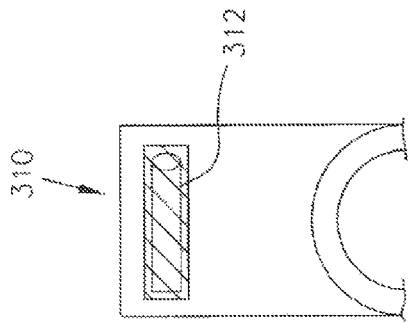
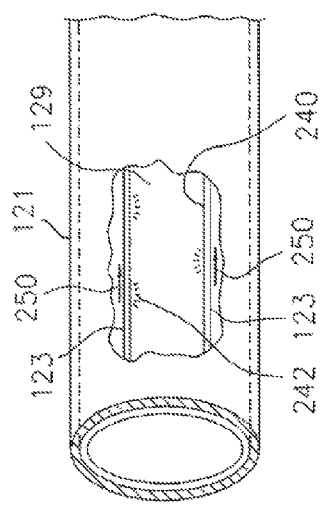
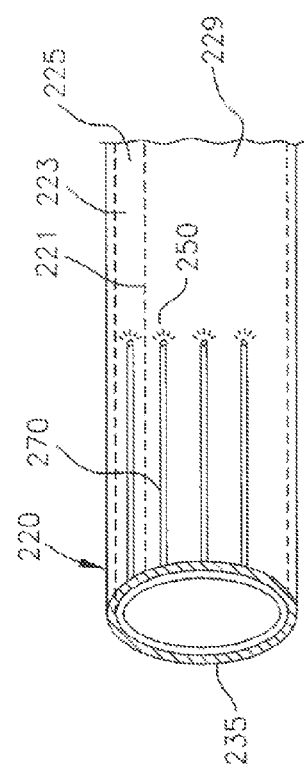

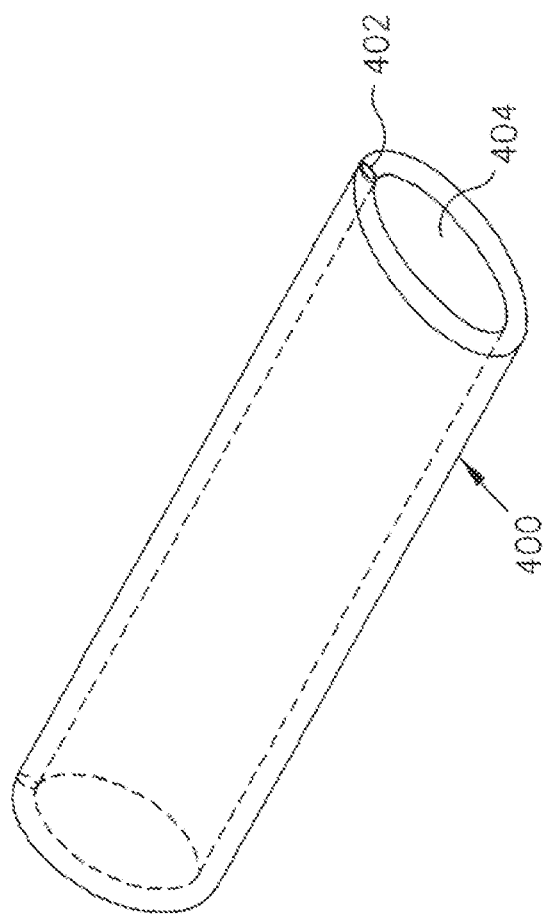

DISPOSABLE, SELF-CONTAINED LARYNGOSCOPE AND METHOD OF USING SAME

REFERENCE TO PENDING APPLICATIONS

This application claims the benefit of U.S. patent application Ser. No. 12/847,915 filed Jul. 30, 2010 entitled Disposable, Self-Contained Laryngoscope and Method of Using Same.

REFERENCE TO MICROFICHE APPENDIX

This application is not referenced in any microfiche appendix.

BACKGROUND OF THE INVENTION

The present invention relates to a laryngoscope, more specifically, toward a disposable laryngoscope having a rigid cylindrical body for clearing, visualizing, and accessing, the intubation pathway.

A laryngoscope is used to assist with the placement of a tube into a patient's trachea to aid with the oxygenation of the patient. The prior art laryngoscope uses either a straight or curved blade that allows for the visualization of the patient's vocal cords which are used for locating the patient's larynx and subsequently the trachea. This reduces the risk of intubating the patients esophagus which would cause air to be blown into the stomach, causing stomach distension and vomiting not to mention depriving the patient of oxygen, and possibly death.

The presence of blood, saliva, vomit secretions can interfere, with the proper placement of the laryngoscope. Further, in emergency situations, the proper placement of the laryngoscope most be done in a quick and safe manner. However, despite good technique by the health care provider utilizing the laryngoscope described in the prior art, there is still a need for an improved laryngoscope that can be used in difficult or emergency situations in and out of a medical facility.

SUMMARY OF THE INVENTION

The present invention satisfies the needs discussed above. The present invention is generally directed toward a laryngoscope, more specifically, toward a disposable laryngoscope having a rigid cylindrical body for clearing and visualizing the intubation pathway to assist with the intubation of a patient in an emergency situation or a patient known for having difficult intubation capability.

One aspect of the present invention includes a laryngoscope having a handle, a cylindrical tube and an optical subassembly. The handle has distal and proximate ends and a cavity for the seating of the optical subassembly. Further, the handle can be configured in a bent or straight configuration. Instruments such as a bougie, damps, tracheal tubes and a suction catheter, can be placed within the interior portion, known as the lumen, of the cylindrical tube included to create an emergency airway kit to be used by emergency medical services inside as well as outside of a medical facility, i.e. a hospital.

The tube is hollow and also has distal and proximate ends. The tube can be cylindrical, oblong or a variation of uniform or non-uniform roundness. The proximate end of the handle is in communication with the proximate end of the tube. An optical subassembly can be located within the handle and can extended into the tube.

The tube also has openings located at its proximate and distal ends. These openings can aid the healthcare provider with visualizing the proper placement of the laryngoscope within the patient's mouth and throat To aid with the insertion of the cylindrical tube, the distal opening is oriented at an angle relative to the vertical cross sectional plane of the tube.

The tube can be made from a metal, a transparent material or translucent material or a combination of the three. The transparent or translucent material will aid in the illumination of the tube along its entire length which will also aid in the proper placement thereof. This is important in those emergency situations where there may be excessive bleeding and/or vomiting which may quickly come up the laryngoscope thereby not obstructing the light source. Further, a suction catheter can be placed within the lumen to assist with the removal of the excessive blood and/or vomit from the patient's airway.

One aspect of the optical subassembly includes a light source located within the handle, a power source such as one or more batteries located also within as handle and in communication with the light source. A light carder such as a fiber optic cable is in communication with the light source and extends from the handle into the tube wherein it produces light so that the healthcare provider can see the tube and into the patient's mouth and throat to aid in the proper placement thereof. In difficult intubation patients or those in art emergency situation, the health care provider passes a bougie through the laryngoscope between the vocal cords and into the trachea. The laryngoscope is removed, and the endotracheal tube (which allows ventilation of the patient) is guided over the bougie Into the trachea to gain safe and quick control of the patient's airway.

Another aspect of the optical subassembly includes a light source providing light down the tube from the proximal end to the distal end. This light will aid the operator in visualizing the larynx despite obstructions such as blood and vomit. In this aspect, as light is conducted through the material of the tube, the tube is illuminated. Further, as light can be provided within the lumen of the tube, interior portion of the tube can also be illuminated. This light will illuminate the circumference of the lumen of the tube.

Another aspect of the present invention includes the tube as described above with the addition of a strip of protective material located along, the tube proximate to its proximate end. The inclusion of this material is to protect the patient's teeth during use. The material can be made from a rubber or other flexible type of material.

Another aspect of the present invention includes the tube as described above further having side ports that can be used for suction and/or jet ventilation.

Another aspect of the present invention includes the laryngoscope tube as described above but is configured to be connectably attached through existing laryngoscope handles. This connection can be swivel and/or hinged and can be removable.

Another aspect of the present invention includes a method of using the laryngoscope tube as described above to secure the airway of a patient. In a difficult or emergency situation where the visualization of a patient's larynx is impaired, the medical provider holds the inventive laryngoscope by the handle and inserts the cylindrical tube into the patient's throat, looking through the cylindrical tube until the larynx is visualized. At that point, a bougie is inserted through the cylindrical tube between the patient's vocal cords and into the patient's trachea. The inventive laryngoscope is removed along the bougie, leaving the bougie in place. The bougie can then guide an endrotracheal tube into the patient's trachea.

Once in place, the bougie is then removed and the endrotracheal tube can be used to ventilate the patient.

Upon reading the included description, various alternative embodiments will become obvious to those skilled in the art. These embodiments are to be considered within the scope and spirit of the subject invention, which is only limited by the claims which follow and their equivalents.

BRIEF DESCRIPTION OF THE DRAWINGS

FIG. 5 is a side view of a second embodiment of the present invention.

FIG. 5A is an exploded side view of the second embodiment of the present invention set out in FIG. 5.

FIG. 6 is a perspective view of an embodiment of the proximate end of the cylindrical tube of the second embodiment of the present invention set out in FIG. 5.

FIG. 7 is a cutaway view of an embodiment of the optical subassembly of the second embodiment of the present invention set out in FIG. 5.

FIG. 7A is a rear view of the proximate end of the cylindrical tube of the embodiment of the present invention set out in FIG. 7.

FIG. 8 is a is a perspective view of a third embodiment of the present invention.

FIG. 9 is a rear view of the proximate end of the cylindrical tube of the third embodiment of the present invention set out in FIG. 8.

FIG. 10 is a perspective view of an additional embodiment of the cylindrical tube of the present invention.

FIG. 11 is a perspective view of an additional embodiment of the cylindrical tube of the present invention.

FIG. 12 is a perspective view of an additional embodiment of the handle of the present Invention.

FIG. 13 is a perspective view of an additional embodiment of the cylindrical tube of the present invention.

DESCRIPTION OF THE PREFERRED EMBODIMENTS

The present invention is generally directed toward a laryngoscope, more specifically, toward a laryngoscope having a rigid cylindrical body for clearing, visualizing, and accessing the intubation pathway.

Figure 1:
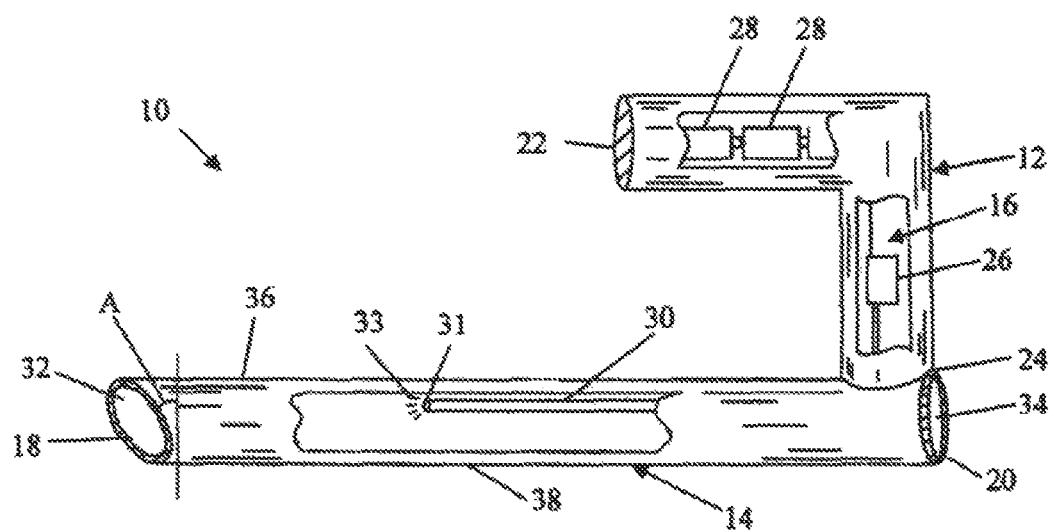
FIG. 1 is a side view of an embodiment of the present invention.

As shown in FIG. 1 the embodiment 10 of the inventive laryngoscope is illustrated. Embodiment 10 comprises a handle 12, a cylindrical tube 14 and an optical subassembly 16 contained within and extending between a handle 12 and cylindrical like 14.

Figure 2:
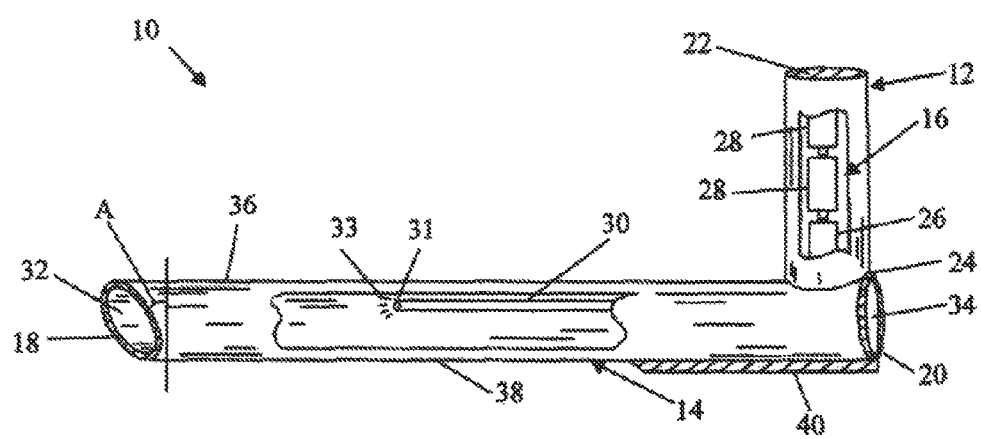
FIG. 2 is a side view of an additional embodiment of the present invention.

Handle 12 has a distal end 22 and a proximate end 24. Handle 12 can have a bent configuration as illustrated in FIG. 1 or a straight configuration as illustrated in FIG. 2.

Cylindrical tube 14 has a distal end 18 having a distal end opening 32 and a proximate end 20 having a proximate end opening. Distal end opening 32 is oriented at an angle relative to the vertical cross sectional plane of cylindrical tube 14. This angling of distal end opening aids in the insertion of cylindrical tube 14 into the patient's mouth and throat. Cylindrical tube 14 is hollow to allow the user to view inside the patient's mouth and throat. The shape of the tube is shown to be cylindrical. This is for illustrative purposes and is not meant to be limiting. The tube can be of various uniform and non-uniform roundness, including oblong, and can have non-uniform radius size from proximate end 20 to distal end 18, and further can be oblong at one end and circular at the other.

Proximate end 20 of cylindrical tube 14 is secured to the proximate end 24 of handle 12. The connection of cylindrical tube 14 and handle 12 can be of a unitary construction or of separate construction.

Optical subassembly 16 includes the light source 26 located within handle 12, a power source 28 located within handle 12 and in communication with light source 26. Power source 28 can include known power sources including batteries. A light carrier 30 is in communication with light source 26 and is located within handle 12 and extends into cylindrical tube 14. Light carrier 30 can include fiber optic cables, light emitting diodes (LEDs) or other similar devices. Light carrier 30 terminates within cylindrical tube 14. Light 33 emanates from the end 31 of light carrier 30. Light 33 illuminates the interior of the cylindrical tube 14 thereby aiding the user of embodiment 10 in placing the embodiment properly within the patient's mouth and throat.

Cylindrical tube 14 is rigid and can be made from a suitable metal, a transparent material, a translucent material or combination thereof. The use of transparent and/or translucent material can aid with the illumination of the entire cylindrical tube 14 along its length. This is useful in situations where blood or other items can hinder the ability to view the interior of the patient's mouth and/or throat. The laryngoscope may be of different lengths and widths.

The laryngoscope may be disposable (or single use), allowing its inclusion with a bougie and suction catheter into an emergency airway kit to be used by emergency medical services inside as well as outside of a medical (hospital) facility. Furthermore, the inventive laryngoscope may be partially disposable. In this situation, the handle portion and optical subassembly portion may be reused while the cylindrical tube portion may be discarded. In such a situation, only the part of the instrument that actually was inserted would be disposed of while the remaining portions would be reused creating a savings on cleaning and replacement costs.

Once the inventive laryngoscope is placed properly within the patient's throat, various devices including a suction tube or a bougie (not shown) can be inserted through cylindrical tube 14 into the patient's trachea. When a bougie is inserted, the cylindrical tube 14 can then be removed by sliding such along the bougie, leaving the bougie in place. The bougie then acts a guide for the proper placement of additional devices such as an endotracheal tube to aid the patient.

Figure 3:
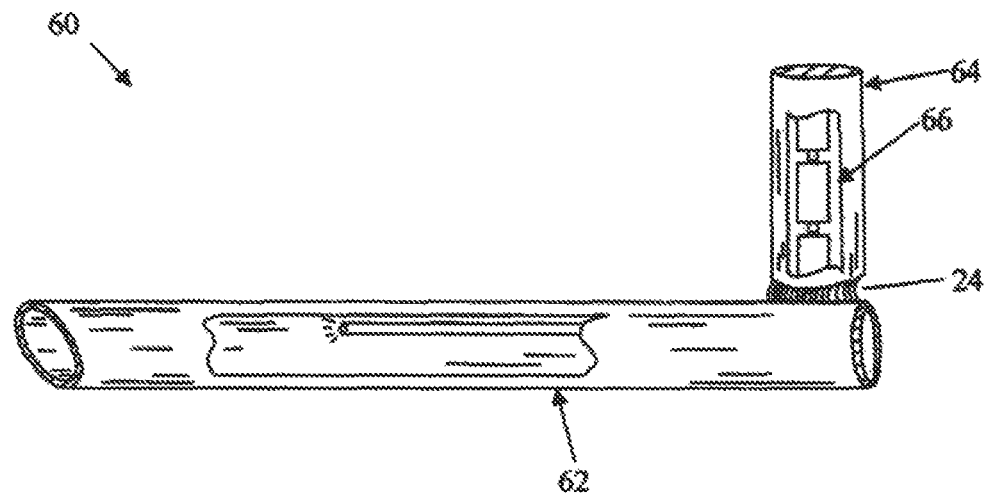
FIG. 3 is a side view of an additional embodiment of the present invention.

Another embodiment 60 of the present invention is illustrated in FIG. 3. This embodiment includes a cylindrical tube 62. Cylindrical tube 62 includes the same features as the cylindrical tube of the previous embodiment. Embodiment 60 also includes a handle 64 and an optical subassembly 66 that is located within handle 64. Handle 64 is hindgely connected to cylindrical tube 62 by a hinge 68. Hinge 6 is merely illustrative and is not limiting. Those schooled in the art would recognize other forms of moveable connections can be utilized with the present invention. Additionally tube 62 can include connection means not shown that can be configured to adapt to prior art laryngoscope handles.

Figure 4:
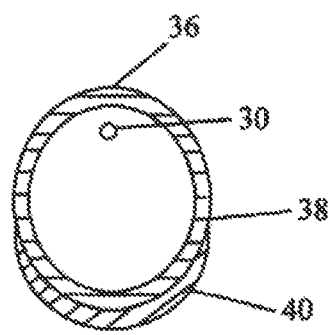
FIG. 4 is a front cross-sectional view of an embodiment of the cylindrical tube of the present invention.

An additional feature of the present invention is illustrated in FIGS. 2 and 4. This feature includes a strip of protective material 40 located, along the outer side 38 at tube 14 near its proximate end 20. This protective material is utilized to protect the teeth and soft tissue located within the patient's mouth during use. The protective material 40 can be made from rubber or other suitable flexible material.

Another feature of the inventive laryngoscope can include a cylindrical tube 14 having one or more side ports not shown to allow for suction and/or jet ventilation.

Another embodiment of the present invention comprises a method of using the laryngoscope tube as described, above to secure the airway of a patient. This embodiment includes holding the inventive laryngoscope by the handle, inserting the cylindrical tube into the patient's throat, looking, through the cylindrical tube until the larynx is visualized. At that point, bougie is inserted through the cylindrical tube between the patient's vocal cords and into the patient's trachea. The inventive laryngoscope is removed along the bougie, leaving the bougie in place. The bougie can then guide an endrotracheal tube into the patient's trachea. Once in place, the bougie is then removed and the endrotracheal tube can be used to ventilate the patient.

Another embodiment 100 of the present invention is illustrated in FIGS. 5-13. Embodiment 100 comprises a handle assembly 110, a cylindrical tube 120 and an optical subassembly 130 extending between the handle assembly 110 and the cylindrical tube 120. Cylindrical tube 120, handle 110 and optical subassembly 130 can be a unitary construction or of separate construction as shown in FIG. 5A. Further, cylindrical tube 120, handle 110 and optical subassembly 130 can be constructed of disposable material.

As shown in FIG. 5, handle assembly 110 has a distal end 112 and a proximate end 114 which is removably secured to optical subassembly 130. Cylindrical tube 120 has a distal end 122 and a proximal end 126 which is removably secured to optical subassembly 130.

Cylindrical tube 120 has an outer surface 121 and an inner surface 123 with a thickness 125 therebetween. The inner surface 123 defines an open passage, known as the lumen 129, which extends the length of the cylindrical tube 120. Distal end 122 of cylindrical tube 120 has a distal end opening 124 providing access to lumen 129. Proximal end 126 has a proximal end opening 128 providing access to lumen 129. Distal end opening 124 can be oriented at an angle A relative to the vertical cross sectional plane at cylindrical the 120. This angling A of distal end opening 124 can aid in the insertion of the cylindrical tube 120 into a patient's mouth and throat.

The cylindrical tube 120 in this embodiment is made from a translucent material. However, one skilled in the art will understand the material from which the cylindrical tube 120 is made can include other types of materials, including non-translucent material and a transparent material. The use of transparent and/or translucent material can aid with the illumination of the entire cylindrical tube 120 along its length. This is useful in situations where blood or other items can hinder the ability to view the interior of the patient's mouth and/or throat. The laryngoscope may be of different lengths and widths.

An embodiment of optical subassembly 130 is shown in the FIGS. 5-7. Optical subassembly 130, having a light source housing 132, is removable secured to cylindrical tube 120 such that the outer surface of optical subassembly 130 is continuous with the outer surface 121. Optical subassembly 130 has an opening 131 that extends the length of optical subassembly 130 and that corresponds to lumen 129. Opening 131 allows for the proper placement of the cylindrical tube 120. The operator peers into opening 131 and through optical subassembly 130 and proximal end opening 128 and looks through lumen 129 and through to distal end opening 124 to see inside the patient's mouth and throat.

A power source 134 is located within handle assembly 110. Within light source housing 132 is a light source 135 that provides light 150 down the cylindrical tube 120 from its proximal end 126 to its distal end 122. This light will aid the operator in visualizing the larynx despite obstructions such as blood and vomit.

This embodiment of light source 135 illustrates a circular light source. This is for illustrative purposes. Those skilled in the art will recognize that other configurations can also be utilized. Light source 135 can be any light source that can project sufficient light into and through cylindrical tube 120, include a solid illuminating light and a ring of light emitting diodes.

In this embodiment, optical subassembly 130 is shown having an inner portion 133. The latter portion 133 directs light 130 into the lumen 129 and thereby illuminating the interior of the cylindrical tube 120.

Other embodiments of optical subassembly 130 allow for light source 135 to project light through the thickness 125 of cylindrical tube 120. In this embodiment, light 150 can illuminate the outer surface 121 and/or the inner surface 123.

When cylindrical tube 120 is constructed of translucent and/or transparent material, light source 135 is capable of illuminating the exterior of cylindrical tube 120 along with within the lumen 129 of the cylindrical tube 120.

Light source 135 is located around the circumference of cylindrical tube 120 at or near its proximal end 126. Light 150 from light source 135 travels along length of cylindrical illuminating the outer surface 121 and/or the inner surface 123 of the cylindrical tube 120. This light will aid the operator in visualizing the larynx despite obstructions such as blood and vomit. This light will illuminate the circumference of the lumen of the tube.

Another embodiment 200 of the present invention is illustrated in FIGS. 8 and 9. In this embodiment, optical subassembly 230 includes a light source housing 232 having a light source 235 located therein. Light source 235 projects light 250 through and within thickness 225 of cylindrical tube 220 between outer surface 221 and inner surface 223. A plurality of light channels 234 are located around the circumference of, and extend the length of, cylindrical tube 220. These light channels 234 extend from the outer surface 221 to the inner surface 223. Light 250 from light source 235 is projected into the plurality of light channels 234. The light 250 then illuminates the outer surface 221 and/or inner surface 223.

Another embodiment of the present invention is shown in FIG. 10. In this embodiment, the inner surface 123 can be coated with an opaque material 240 to cut down on the glare from the light being projected therein. When opaque material 240 is used with cylindrical tube 120, openings 242 within opaque material 240 are positioned around the circumference and length of the inner surface 123. These openings 242 allow for light 250 to penetrate into the lumen 129 of the cylindrical tube 120. This coating can also act to avoid glare into the operator's eye.

Another embodiment of the present invention is shown in FIG. 11. In this embodiment, fiber optic lines 270 extend from light source 235 and through the thickness 225 of cylindrical tube 220 between outer surface 221 and inner surface 223. These fiber optic lines allow for light 250 to illuminate the outer surface 221 and/or inner surface 223, along with the lumen 229 along the length of cylindrical tube 220.

As illustrated in FIG. 13, another embodiment of the present invention comprises a handle assembly (not shown), a cylindrical tube 400 and an optical subassembly as previously described (not shown) along with the inclusion of a side tube 402 to allow ventilation of the patient using general anesthesia equipment. The side tube has an elongation such that it can pass through between the vocal cords into the trachea to become a "ventilating bronchoscope". The side tube 402 can be secured to the cylindrical tube 400 and/or handle assembly through standard securing means and processes. Additionally, side tube 402 can be located within the lumen 404 of cylindrical tube 400. In all cases, however, the opening of side tube 402 at the proximal end of cylindrical tube 400 will always be located on the outside of cylindrical tube 400 to accommodate instruments, attachments and other tools.

Another embodiment 110 of the optical subassembly 130 of the present invention as described above along with the inclusion of a toggle switch 312 to allow the turning off and on the light source connected thereto, along with having the ability to dim or increase the amount of illumination provided the optical subassembly. Those skilled in the art will recognize that any light switch mechanism can be utilized to both control light intensity and/or provide power to the optical subassembly. Such light switch mechanisms can include slide switches. Further since this embodiment can be disposable, the light switch mechanism can include a single pull strip that engages the appropriate circuitry to allow power to be provided optical subassembly 130 such that once activated the power will not be disengaged until the power source is drained. The descriptions of the various light switch mechanisms in this description are merely illustrative and are not meant to be limiting.

While these embodiments describe the present invention in terms of a laryngoscope to be used within the throat area of a patient, such description is illustrative. Those skilled in the art will recognize that the present invention described herein can be utilized with any body cavity or orifice for examination of those areas. The description of the use within the throat region is not meant to be limiting.

While the invention has been described with at certain degree of particularity, it is manifest that many changes may be made in the details of construction and the arrangement of components without departing from the spirit and scope of this disclosure. It is understood that the invention is not limited to the embodiments set forth herein lair purposes of exemplification, but is to be limited only by the scope of the attached claims, including the full range of equivalency to which each element thereof is entitled.

I claim:

1. A laryngoscope comprising:
   a handle assembly and a power source mounted within said handle assembly, said handle assembly having a distal end and a proximate end wherein said proximate end is secured to an optical subassembly;
   said optical subassembly comprising a light source coupled to the power source and a housing supporting the light source, said housing having an opening extending along its length;
   a tube having an outer surface, an inner surface, a distal end and a proximate end defining a lumen there through, the proximate end of said tube being secured to the housing such that the opening in the housing aligns with the lumen, said tube having one or more longitudinal channels for guiding light from its proximate end to its distal end; and
   wherein the light source is positioned around the opening in the housing and arranged to project light from the proximate end of said tube through said longitudinal channels to the distal end of the tube to illuminate a length of the tube.

2. The laryngoscope of claim 1 wherein the light source is a circular light source.

3. The laryngoscope of claim 2 wherein the light source comprises a ring of light emitting diodes.

4. The laryngoscope of claim 1 wherein the tube is made from a metal.

5. The laryngoscope of claim 1 wherein the tube is made from a transparent material.

6. The laryngoscope of claim 1 wherein the tube is made from a translucent material.

7. The laryngoscope of claim 1 wherein the tube is made from a combination of two or more of the group consisting of metal, transparent material and translucent material.

8. The laryngoscope of claim 1 wherein the one or more longitudinal channels are configured to guide light from the inner surface of the tube to the outer surface of the tube.

9. The laryngoscope of claim 1 wherein the one or more longitudinal channels comprise fiber optic lines imbedded within the defined thickness of the tube to carry light along the length of the tube.

* * * * *